(12) United States Patent
Pantalos et al.

(10) Patent No.: US 11,540,858 B2
(45) Date of Patent: Jan. 3, 2023

(54) MULTI-LUMEN ARTHROSCOPY CANNULA (MLAC) AND METHODS OF USE

(71) Applicant: University of Louisville Research Foundation, Inc., Louisville, KY (US)

(72) Inventors: George Pantalos, Louisville, KY (US); Justin Heidel, Burlington, KY (US); David Caborn, Louisville, KY (US)

(73) Assignee: University of Louisville Research Foundation, Inc., Louisville, KY (US)

(*) Notice: Subject to any disclaimer, the term of this patent is extended or adjusted under 35 U.S.C. 154(b) by 515 days.

(21) Appl. No.: 16/655,835

(22) Filed: Oct. 17, 2019

(65) Prior Publication Data
US 2020/0121358 A1    Apr. 23, 2020

Related U.S. Application Data

(60) Provisional application No. 62/746,604, filed on Oct. 17, 2018.

(51) Int. Cl.
*A61B 1/317*    (2006.01)
*A61B 17/34*    (2006.01)

(52) U.S. Cl.
CPC .......... *A61B 17/3421* (2013.01); *A61B 1/317* (2013.01); *A61B 2017/3449* (2013.01); *A61B 2217/005* (2013.01); *A61B 2217/007* (2013.01)

(58) Field of Classification Search
CPC ............ A61B 17/3421; A61B 17/3462; A61B 2217/005; A61B 2217/007; A61B 1/317
See application file for complete search history.

(56) References Cited

U.S. PATENT DOCUMENTS

| 4,654,030 A | 3/1987 | Moll et al. |
| 5,779,697 A * | 7/1998 | Glowa ............... A61B 17/3462 606/185 |

(Continued)

FOREIGN PATENT DOCUMENTS

| WO | 93/11699 | 6/1993 |
| WO | 2016/089828 A1 | 6/2016 |

OTHER PUBLICATIONS

VerasOne Blunt Trocar Access System. Metronic. Jun. 2018.

*Primary Examiner* — Deanna K Hall
(74) *Attorney, Agent, or Firm* — WCF IP

(57) ABSTRACT

A multi-lumen arthroscopy cannula (MLAC) is described which may be used to contain and manage joint irrigation fluid as a means of improving the state of arthroscopic surgery. The MLAC includes an arrangement of components within a cannula housing. An internal passage (central lumen) through which surgical instruments may be inserted into the body includes a series of components which greatly reduce the leakage path of fluid through the central lumen while enabling manipulation of surgical instruments during arthroscopic procedures. A dual-tapered diaphragm seal grips the instruments as it is manipulated to prevent leakage. This works in concert with the consecutively placed multi-leaflet valves, which act to prevent internal leakage and maintain pressure within the surgical cavity. Unique features of this cannula, aside from the multiple valves and dual-tapered diaphragm seal, include bilateral lumens which provide infusion and withdrawal of irrigation inside the joint capsule. Complementary to this is an elongated central lumen which accommodates both straight- and curved-tip arthroscopic instruments.

20 Claims, 14 Drawing Sheets

(56) References Cited

U.S. PATENT DOCUMENTS

| | | |
|---|---|---|
| 6,808,505 B2 | 10/2004 | Kadan |
| 9,101,701 B2 | 8/2015 | Kumar et al. |
| 9,554,788 B1 | 1/2017 | Redler |
| 9,675,379 B2 | 6/2017 | Kucklick |
| 10,085,768 B2 | 10/2018 | Kucklick |
| 2004/0082915 A1 | 4/2004 | Kadan |
| 2005/0234298 A1* | 10/2005 | Kucklick ........... A61B 17/3423 600/156 |
| 2016/0331401 A1 | 11/2016 | Dreyfuss et al. |

* cited by examiner

Section 5-5

Section 13-13

MULTI-LUMEN ARTHROSCOPY CANNULA (MLAC) AND METHODS OF USE

CROSS-REFERENCE TO RELATED APPLICATIONS

This application claims benefit of U.S. Provisional Application No. 62/746,604, filed Oct. 17, 2018, the complete contents of which are hereby incorporated by reference.

FIELD OF THE INVENTION

The invention generally relates to a system for performing an arthroscopic surgical procedure. The invention is particularly suited to allowing irrigation and suction during a surgical procedure to maintain joint cavity pressure and clear the surgical field.

BACKGROUND

Arthroscopy is a minimally invasive surgical procedure on a joint in which repair of damage, revision of tissue, or replacement of a joint component is performed through a small incision with specially designed surgical tools. It is technically possible to do an arthroscopic examination of almost every joint, but is most commonly used for the knee, shoulder, elbow, wrist, ankle, foot, and hip. Arthroscopy is particularly useful for exploratory procedures to diagnose and repair abnormalities. For instance, meniscus repair, ACL reconstruction and other repairs of knee damage or abnormality are frequently performed using arthroscopic surgery. One advantage over traditional open surgery is that the joint does not have to be opened up fully. This reduces recovery time and may increase the rate of success due to reduced trauma to the connective tissue. Thus, arthroscopy is generally preferred over traditional surgery due to the body of evidence documenting faster healing and post-surgical recovery times with less scarring.

In general, arthroscopic surgical instruments are smaller than traditional instruments, being specially designed to access and manipulate the surgical target via the small incision sites. For instance, knee arthroscopy is typically performed through two small incision sites, one for the arthroscope and one for the surgical instruments to be used in the knee cavity. In some instances, the surgical tools fit through a lumen of the arthroscopic device in which the access ports can be even more restricted in size. In addition to surgical instruments, an endoscopic camera is inserted into the surgical site so that the joint area can be viewed on a video monitor. An irrigation fluid, such as saline, is used to distend the joint and make a surgical space. The irrigation fluid needs to be suctioned periodically to clear the visual field of the site. The competing needs of irrigation/distention and suction/clearing must be carefully balanced for optimal maintenance of the surgical site during a procedure.

One example arthroscopy tool is the diagnostic needle arthroscopy and lavage system described in U.S. Pat. No. 6,808,505. Disclosed is a system for performing a diagnostic needle arthroscopy and lavage through a single incision and entry port into the joint compartment. A central lumen provides access for surgical tools, and two additional concentric offset channels for fluid surround the central lumen. A handpiece has valves for irrigation and suctioning through the two concentric off-set channels, so that irrigation fluid is delivered and removed through the handpiece. The system also includes a biopsy cannula that can be exchanged for a diagnostic cannula. The biopsy cannula also comprises a pair of piggyback cannulas, one for visualization, diagnosis, irrigation and suction, while the other is for insertion of a biopsy instrument or surgical device.

WO 1993011699A1 teaches a multi-function arthroscope having a laser channel, an irrigation tube and a suction tube, as well as optical fibers housed within a sleeve and tubular sheath. The multi-function arthroscope can be used to perform laser surgery, irrigate with saline, suction saline and vacuum debris in a single insertion though a single incision. An external source of saline solution is under positive pressure in conjunction with a source of negative pressure for suctioning.

U.S. Pat. No. 9,554,788 teaches a method and apparatus for securing an arthroscopic cannula in place during arthroscopic surgery to mitigate leakage of fluid from the joint and seepage of the fluid into surrounding tissue. A further advantage is that reducing leakage of fluid during arthroscopic surgery reduces consumption of saline while simultaneously reducing stiffening of the joint due to seepage into surrounding tissues, and decreasing the likelihood of expulsion of the cannula under pressure from the joint. These aspects are of further benefit because reducing expansion of surrounding soft tissue decreases complications and improves patient recovery. A further benefit is enhancing safety in the operating room by reducing accumulation of fluid on the floor.

Other examples of arthroscopic tools with limited function are known. U.S. Pat. No. 4,654,030 is a trocar assembly with a single stopcock for insufflation of gas to expand the surgical field. U.S. Pat. Nos. 9,675,379 and 10,285,768 show an arthroscopic flexible portal cannula device and delivery system having a single port for liquid irrigation and suction. US2016/0331401 is an arthroscopy cannula with one or more inflatable components to maintain fluid pressure at an incision point through which arthroscopic instruments may be manipulated. Independent pump systems, such as that of U.S. Pat. No. 9,101,701, are typically used to provide continuous flow irrigation and/or suctioning of saline or other liquids during an arthroscopic procedure. Various trocar assemblies for laparoscopic surgeries share similar features with arthroscopic devices, including a port for irrigation, insufflation and/or suctioning, an obturator within a bore for insertion of laparoscopic instruments, and outer sheath component, and various means for secure placement. An assortment of these are commercially available from surgical device companies, including Medtronic, EvoMed, Stryker and Storz.

SUMMARY OF THE INVENTION

While each of the arthroscopic devices described in the preceding section perform useful functions, none of the devices is able to provide a single port of entry for surgical tools and an arthroscope, plus provide dual ports for irrigation and suction while maintaining steady positive pressure in the joint compartment without leakage of the irrigation fluid. A multifunctional arthroscopic tool with these features would improve surgical precision for surgical practitioners and outcome for patients. There is currently no product on the market that fulfills all these needs. An objective of embodiments of the instant disclosure is to overcome some or all of these concerns.

Embodiments include a multi-lumen arthroscopic cannula and methods for its use. Some embodiments are tools for performing arthroscopic surgery. Embodiments are particularly suited to allowing simultaneous irrigation and suction of a fluid during a surgical procedure to maintain joint cavity pressure and clear the surgical field.

Embodiments of a multi-lumen arthroscopy cannula (MLAC) described herein may be used to contain and manage joint irrigation fluid as a means of improving the state of arthroscopic surgery. An arrangement of components is provided within a cannula housing. The internal passage (central lumen), through which the surgical instrument is inserted into the body, comprises a series of components which greatly reduce the leakage path of fluid through the central lumen, enabling manipulation of surgical instruments during arthroscopic procedures. Some exemplary central lumen and component assemblies are described in WO2016089828A1 (PCT/US2015/063125), corresponding to US 2017/0360476 A1 (U.S. Ser. No. 15/524,115); these prior publications are incorporated herein by reference. A dual-tapered diaphragm seal grips the instrument shaft as it is inserted, manipulated, and withdrawn to prevent leakage. The diaphragm seal works in concert with consecutively placed multi-leaflet valves, which act to prevent internal leakage and assist in maintaining pressure within the surgical cavity with instrument insertion and withdrawal.

Unique to exemplary cannulas described herein are bilateral lumens which provide infusion and withdrawal of irrigation fluid inside the joint capsule. The bilateral lumens are complementary to an ellipsoid central lumen which accommodates both straight- and curved-tip arthroscopic instruments. All three lumens form a unitary structure that extends into the patient during surgery to provide simultaneous instrument access, fluid infusion, and fluid withdrawal.

In some embodiments, incorporated into the cannula housing are bilateral Luer lock-style ports, one for the irrigation lumen and the other for the suction lumen. The ports narrow to channels which travel to the distal end of the cannula, along the shaft, which is inserted into the patient's joint. This allows for simultaneous suction and irrigation of saline solution during the procedure to maintain joint cavity pressure while periodically clearing the surgical field.

DETAILED DESCRIPTION

Figure 1:
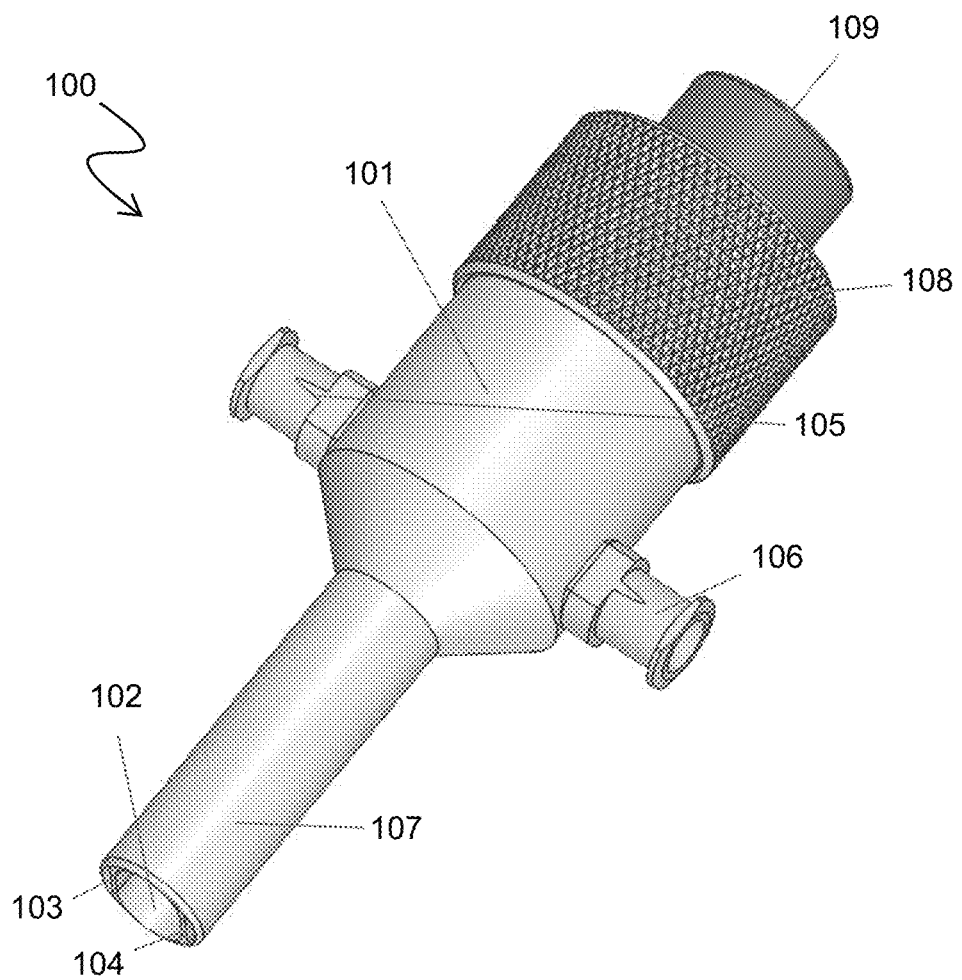
FIG. 1 is a perspective view of an exemplary multi-lumen arthroscopy cannula (MLAC).
Figure 2:
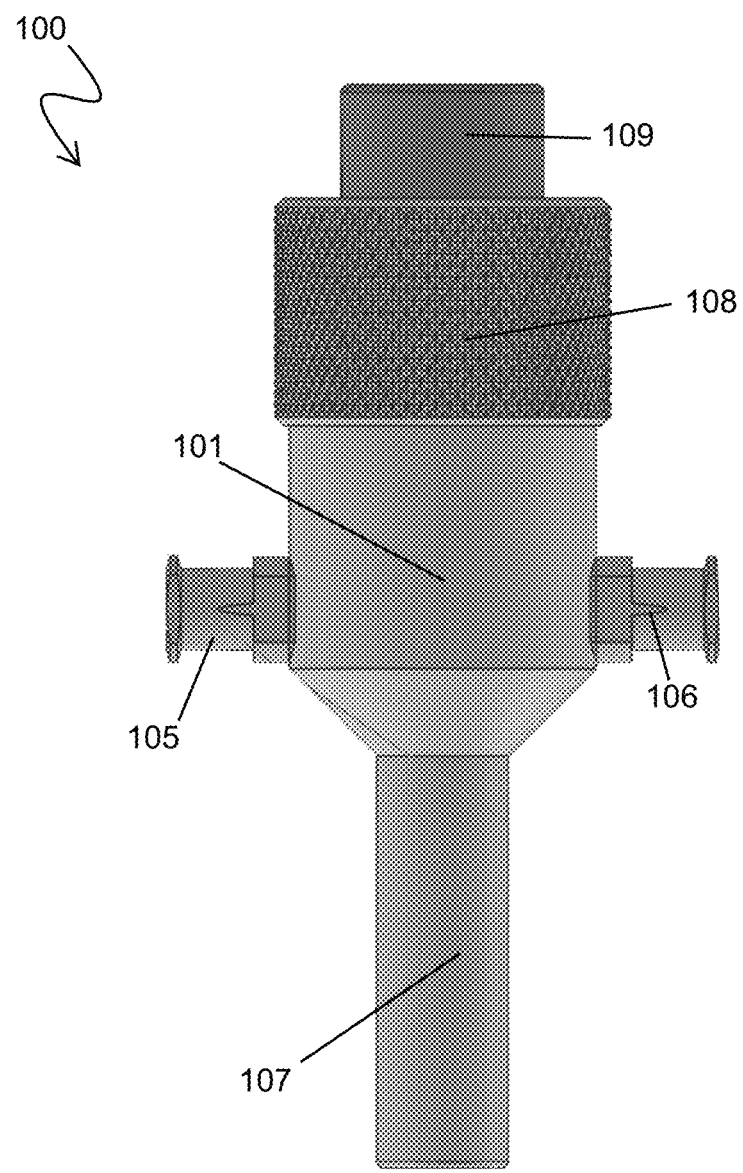
FIG. 2 is a first side view of the MLAC.
Figure 3:
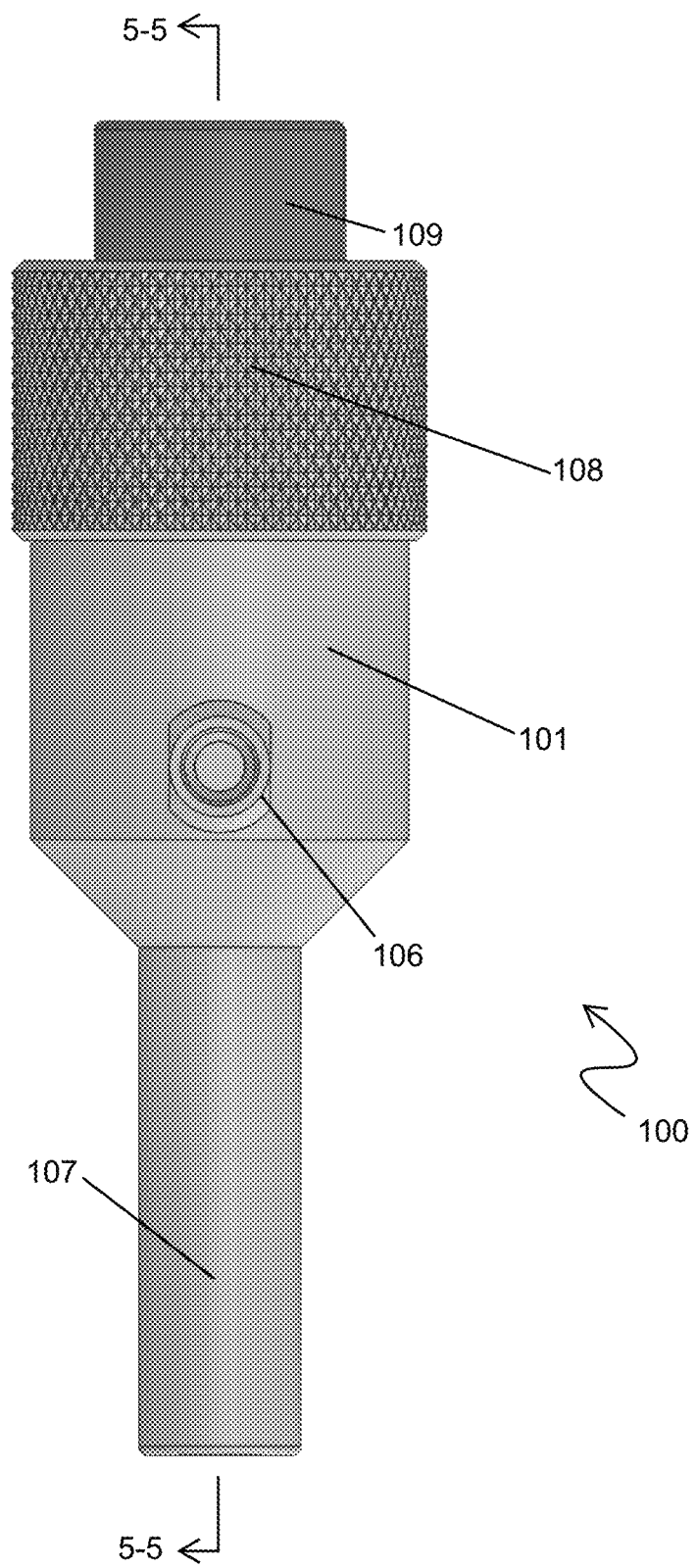
FIG. 3 is a second side view of the MLAC.

FIGS. 1, 2, and 3 show alternative external views of a fully-assembled multi-lumen arthroscopy cannula (MLAC) 100. MLAC 100 comprises a cannula housing 101, an end cap 108, and a dual-tapered diaphragm seal 109. The cannula housing 101 comprises a cannula shaft 107 the space within which is partitioned into a central lumen 102 and bilateral fluid channels 103 and 104. Channel 103 may be an irrigation channel while channel 104 is a suction channel, or vice versa. The bilateral fluid channels 103 and 104 connect to respective ports 105 and 106, which for purposes of this disclosure are generally described as Luer-style ports. Alternative types of ports may be used in some embodiments. The Luer-style ports 105 and 106 are positioned above the cannula shaft, at a lower part of the cannula housing 101, e.g., at a base of the main body of the cannula housing. The ports may be respectively connected with tubing to an external source of saline solution under positive pressure or a source of negative pressure for suctioning.

For purposes of this disclosure, the distal end of the MLAC 100 may be referred to as the lower end of the device, whereas the proximal end of the MLAC 100 may be referred to as the upper end. Accordingly, the dual-tapered diaphragm seal 109 is at the proximal/upper end, whereas the distal openings of the central lumen 102 and bilateral fluid channels 103 and 104 are at the distal/lower end.

Figure 4:
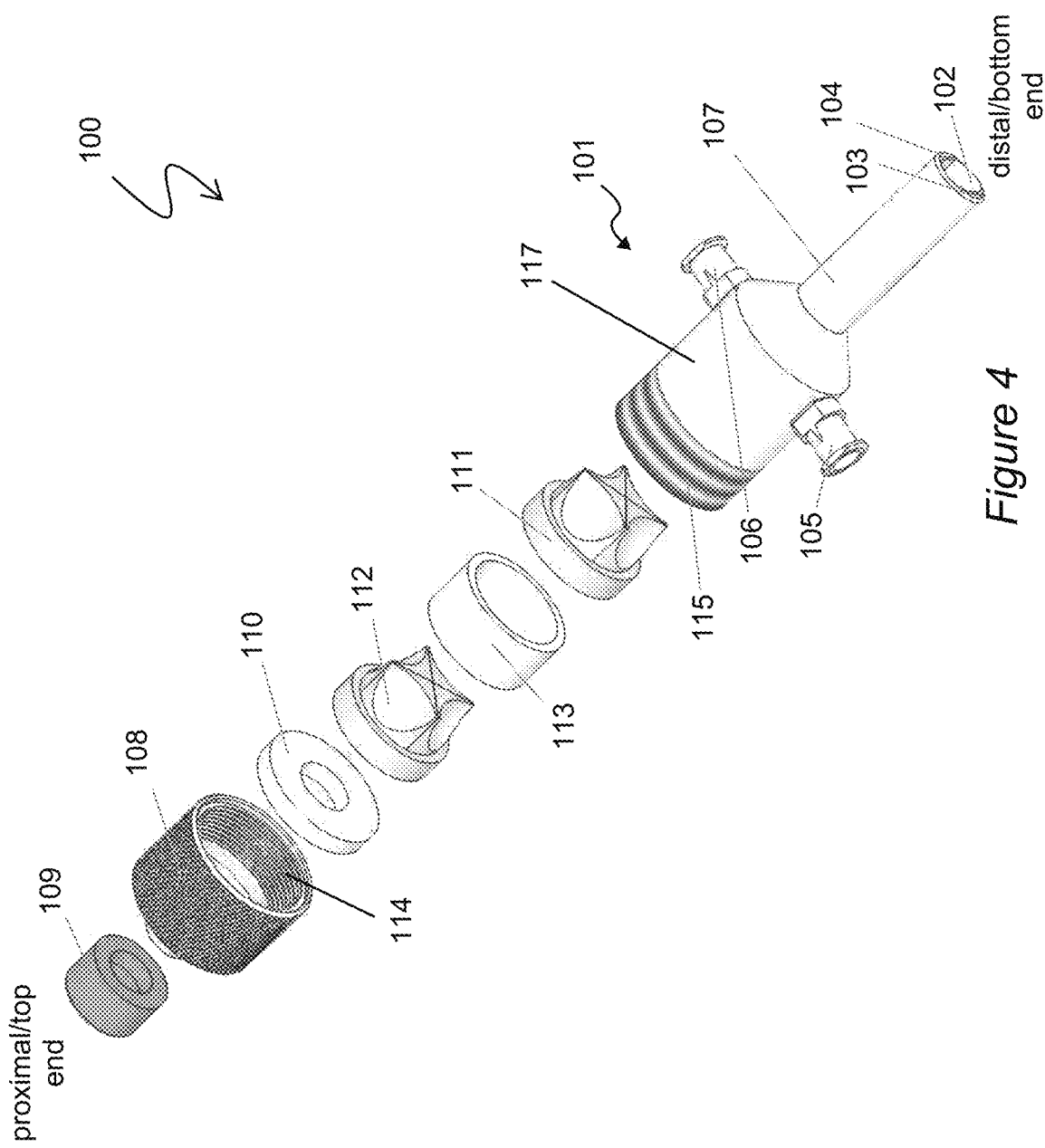
FIG. 4 is an exploded view of the MLAC.

FIG. 4 is an exploded view of MLAC 100. When assembled, the end cap seal 110, multi-leaf valve 112, valve spacer 113, and multi-leaflet valve 111 are arranged in series together within the cannula housing 101, between the proximal end of the end cap 108 and the proximal end of the cannula shaft 107.

An MLAC 100 may be single use and disposable or recyclable, or it may be re-used, depending on the particular embodiment. For general assembly and disassembly (e.g., in the case of re-use), a threaded connection between threading 114 of end cap 108 and threading 115 of cannula housing 101 is all that need be undone in order to remove the end cap seal 110, multi-leaf valve 112, valve spacer 113, and multi-leaflet valve 111 for cleaning or replacement. The end cap seal 110, multi-leaf valve 112, valve spacer 113, and multi-leaflet valve 111 are all aligned to share a common center axis of symmetry with the cannula housing 101.

Figure 5:
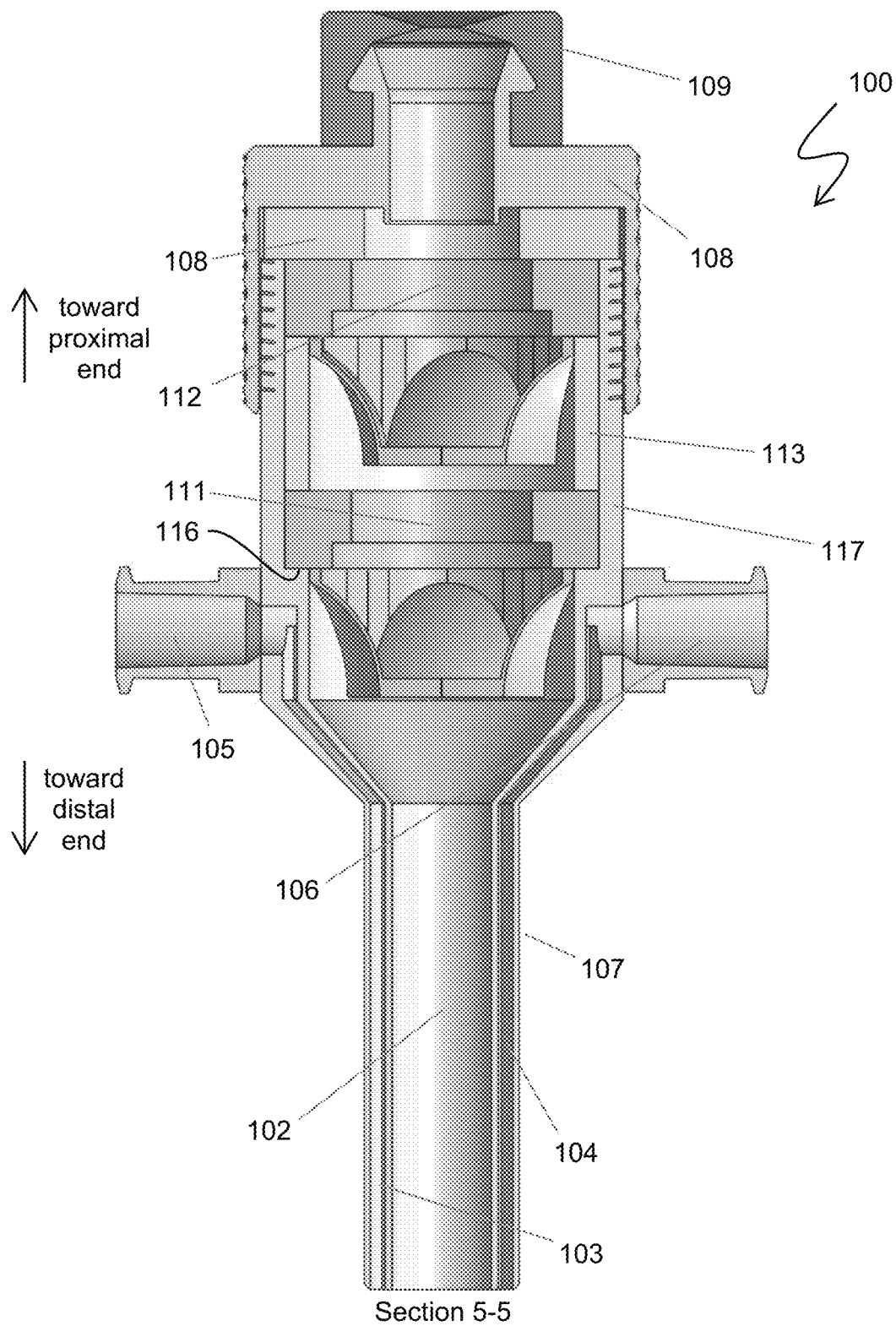
FIG. 5 is a cross-sectional view of the MLAC taken at line 5-5 from FIG. 3.

FIG. 5 is a longitudinal cross-sectional view taken along line 5-5 of FIG. 3. The MLAC 100 is fully assembled in this view. Of the removable internal components to the cannula housing, the multi-leaflet valve 111 is the bottommost component. The multi-leaflet valve 111 is held in place at the bottom end by an annular retention ledge 116 at a distal end of the main cavity within cannula housing 101. Part of the valve with an outer diameter smaller than the inner diameter of the retention ledge 116 protrudes past the retention ledge 116. The protruding part is co-positioned along the longitudinal axis with the Luer-style ports 105 and 106. The ports 105 and 106 are positioned on opposite sides of the cannula housing 101.

The central lumen 102 extends at least the full length of the cannula shaft 107. When the valves 111 and 112 open, as when permitting passage of one or more surgical instruments or scopes, the central lumen 102 extends in effect from end-to-end of the MLAC 100. That is, the central lumen 102 may be treated as extending from the proximal end through the distal end. The central lumen 102 is thus responsible for permitting a surgical instrument or scope to enter the MLAC 100 at the proximal end through the seal 109 and exit the MLAC 100 through the distal opening of the central lumen 102. The cannula shaft 107 length (and correspondingly, the central lumen 102 length within the cannula shaft 107) may be, for example 3 cm, or in a range from 2 to 6 cm to cover the range from smaller pediatric patients to larger adult patients. The relatively short length provides greater flexibility in the types of instruments, such as curved-tip instruments, which may be passed through the central lumen 102. The cannula housing 101, and in particular the cannula shaft 107, may be made of a clear or transparent material, such as a clear medical grade plastic.

Figure 6:
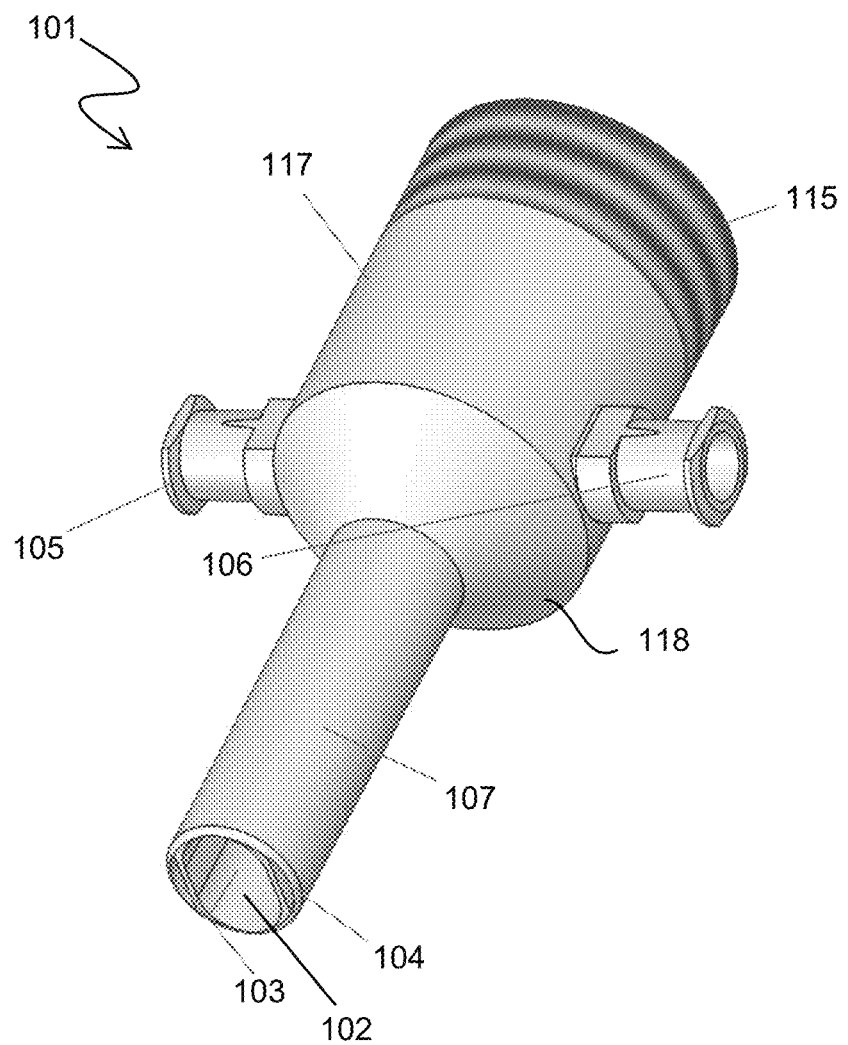
FIG. 6 is a perspective view of an exemplary cannula housing.
Figure 7:
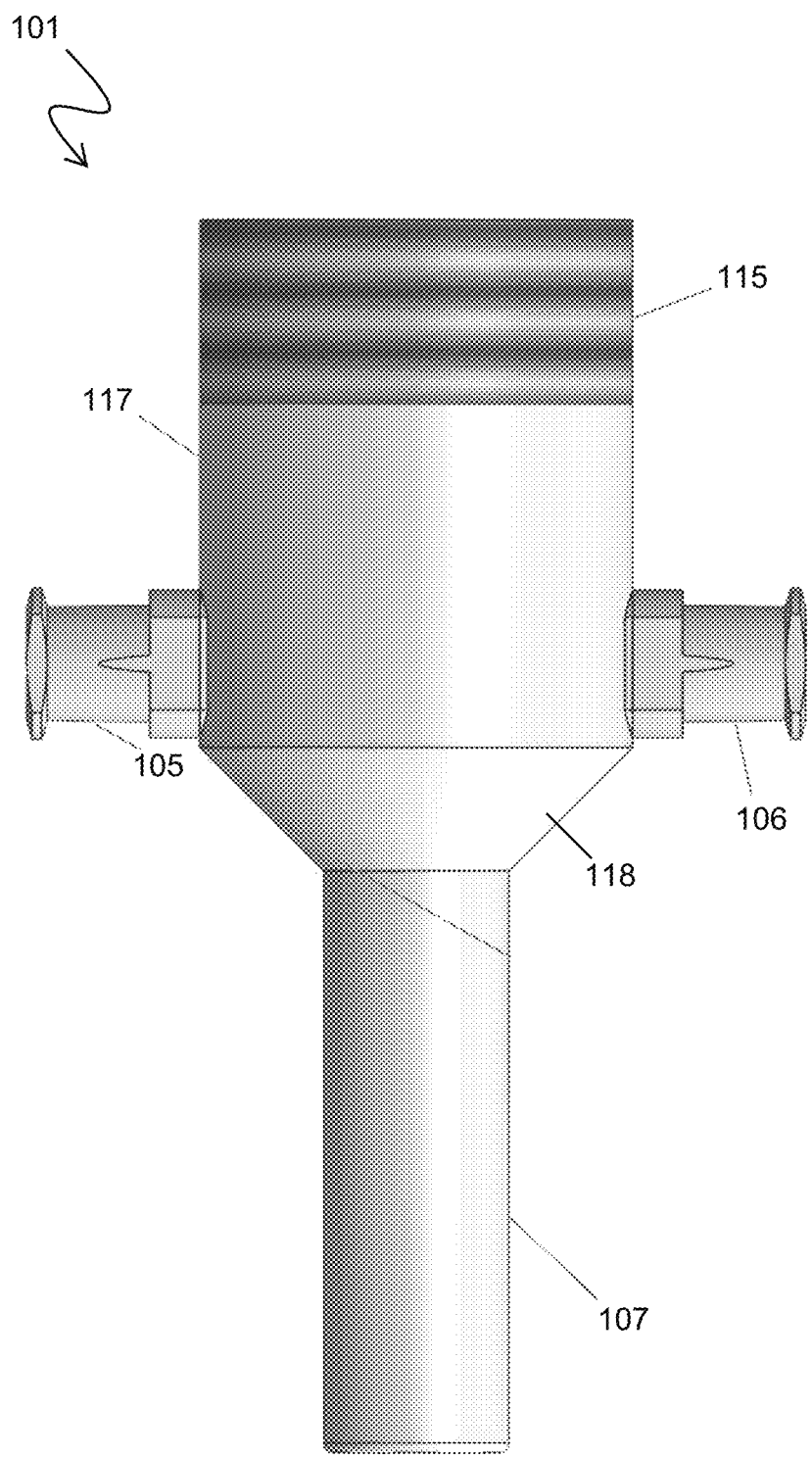
FIG. 7 is a side view of the cannula housing.

FIGS. 6 and 7 are alternative exterior views of only the cannula housing 101, independent of the other components of MLAC 100. The cannula housing 101 includes two main parts. At the proximal end is a main body 117, and at the distal end is a cannula shaft 107. The main body 117 may consist of a cylinder of constant diameter for a center portion thereof, threading 115 at a proximal end, and a tapered portion 118 at a distal end. The tapered portion 118 provides a gradual transition from the main body 117 to the cannula shaft 107.

Figure 8:
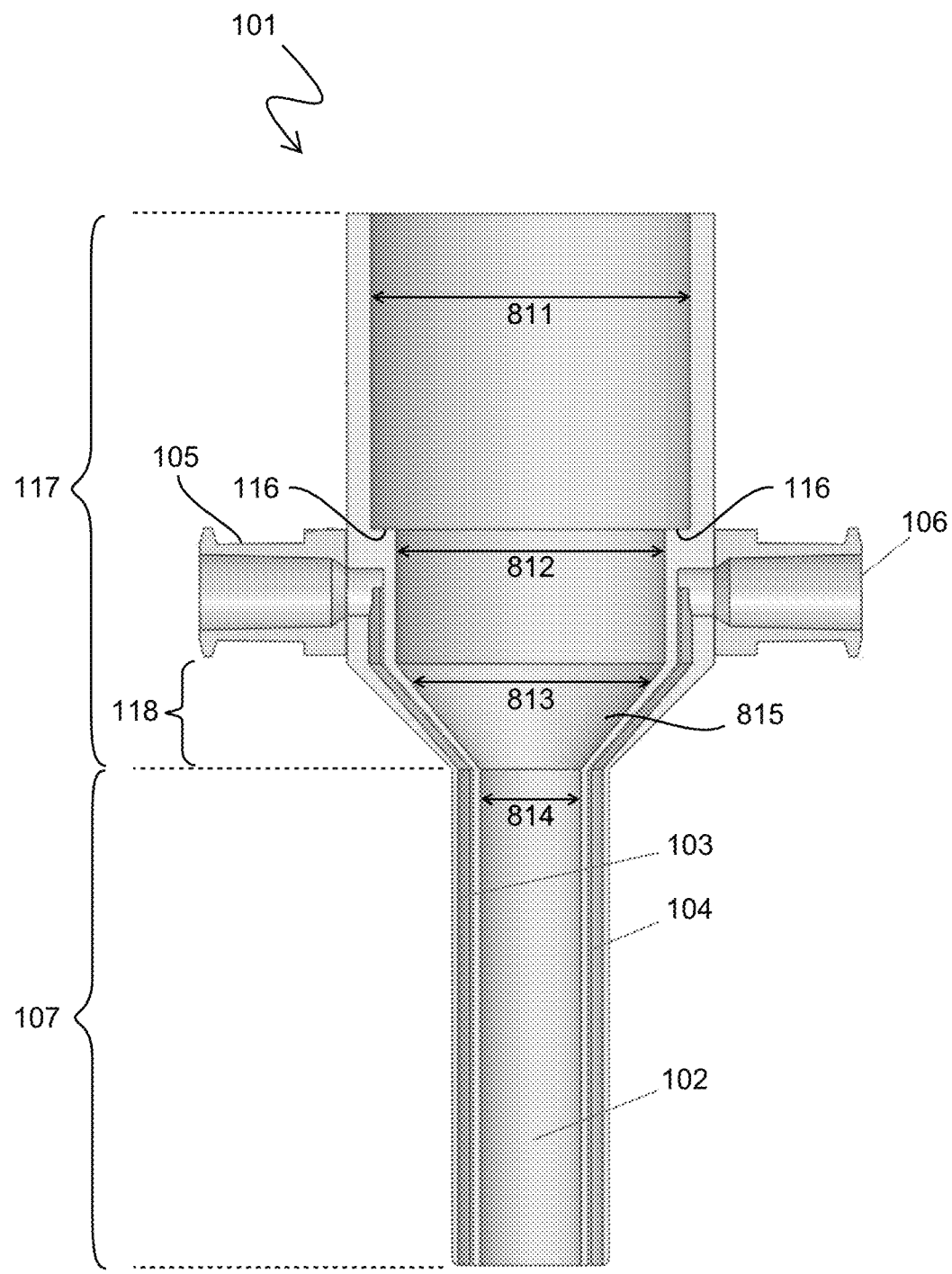
FIG. 8 is a cross-sectional view of the cannula housing.

FIG. 8 shows a longitudinal cross-sectional view of the cannula housing 101. As discussed above, the cannula housing 101 comprises a main body 117 and a cannula shaft 107. The main body 117 includes a tapered portion 118 that transitions the shape/size of the main body 117 to the shape/size of the cannula shaft 107.

The main body 117 has a first cylindrical cavity with an inner diameter 811. The main body 117 has a second cylindrical cavity contiguous with the first, but with a reduced inner diameter 812. The two contiguous cavities are symmetrically aligned about the center longitudinal axis of the cannula housing 101. At the plane where the two cavities meet, and thus where a sharp change in inner diameter occurs, is annular retention ledge 116.

In the tapered portion 118 of the main body 117, the inner diameter 813 gradually reduces as it extends in the distal direction. The tapered portion 118 has an inner diameter 813 which gradually transitions from the inner diameter of the main body 117 (at the main body's distal end) to the inner diameter of the central lumen (at the central lumen's proximal end). Inner diameter 813 equals reduced inner diameter 812 of main body 117 at one end; inner diameter 813 equals width 814 of the cannula shaft 107 at the other end. As a result of the gradual change in diameter, tapered portion 118 may have a conical or approximately conical inner surface 815. (Figures discussed below show that a cross-section of the bottom of the "cone" may be oblong rather than a true circle, owing to the ellipsoid shape of the central lumen with which the tapered portion 118 is configured to mate.) The gradual transition in diameter 813 helpfully guides instruments passed through the MLAC 100 into the central lumen 102 without the end getting caught or stuck on a ledge or corner. That is to say, tapered portion 118 results in there being no ledge or corner on which a surgical instrument may get stuck.

The cannula shaft 107 is configured for insertion into a patient. Consistent with the essential purpose of trocars, the central lumen 102 of the cannula shaft 107 provides a pathway into the body for operating instruments. Appreciably different from trocars in general, however, is the arrangement of fluid channels 103 and 104 on opposite sides of the central lumen. The fluid channels 103 and 104 are integrated with the central lumen 102. For example, a single wall serves the dual functions of serving as a side of the central lumen 102 and a side of the fluid channel 103. Another single wall serves the dual functions of serving as a side of the central lumen 102 and a side of the fluid channel 104. The fluid channels 103 and 104 run parallel with the central lumen 102.

The integration of the bilateral fluid channels 103 and 104 into the cannula shaft 107 provides unique benefits over existing cannulas for arthroscopic surgeries. Prior to present embodiments, irrigation and withdrawal (suction) tubules, if desired, may have had to be supplied through a central lumen shared with surgical instruments. The tubules may have risked entanglement with the instruments and may not be reliably positioned. Alternatively, fluid may have been supplied through the central lumen; in this case the lack of at least two separated channels meant fluid could not be simultaneously delivered and removed. By contrast, the instant embodiment's integration of the fluid channels within the structure defining the central lumen (the cannula shaft) avoids these problems entirely.

A central objective of the assembly including the dual-tapered diaphragm seal 109 and multi-leaflet valves 111 and 112 is to limit if not substantially prevent egress of fluids from the surgical field through the MLAC 100. Were infusion and withdrawal tubules required to pass through seal 109 and valves 111 and 112 in like manner to the surgical instruments, the numerosity of elements passing through poses a heightened risk of fluid and pressure loss from the surgical sight. In the MLAC 100, these risks and problems are averted. The fluid supplied to or withdrawn from the surgical site enters or exits the MLAC 100 through the dedicated ports 105 and 106. The ports 105 and 106, being wholly apart from the central lumen passage that extends through the dual-tapered diaphragm seal 109 and multi-leaflet valves 111 and 112, ensure that the delivery and withdrawal of fluid to the surgical sight has no effect on the means by which the MLAC 100 provides a seal about the surgical instrument. The instrument 100 permits fluid to be delivered to and withdrawn from the surgical field whilst only surgical instruments, in some cases only a single surgical instrument, and nothing else is passed through the dual-tapered diaphragm seal 109 and valves 111 and 112.

To whatever extent some fluid and therefore pressure may escape the surgical sight through the central lumen, the flow rates of liquids in the bilateral fluid channels 103 and 104 may be varied to compensate for the loss, thereby maintaining a desired pressure. For example, in the event of fluid loss through the central lumen, the rate of flow of suction channel (103 or 104) may be reduced, and/or the rate of flow of the effusion channel (104 or 103) may be increased. The rates of suction and effusion may also be varied up or down concurrently to provide faster or slower, as the case may be, irrigation and washing of the surgical field. The use of two critically positioned, multileaflet valves minimizes the possibility of central lumen leakage after an instrument is withdrawn.

Figure 9:
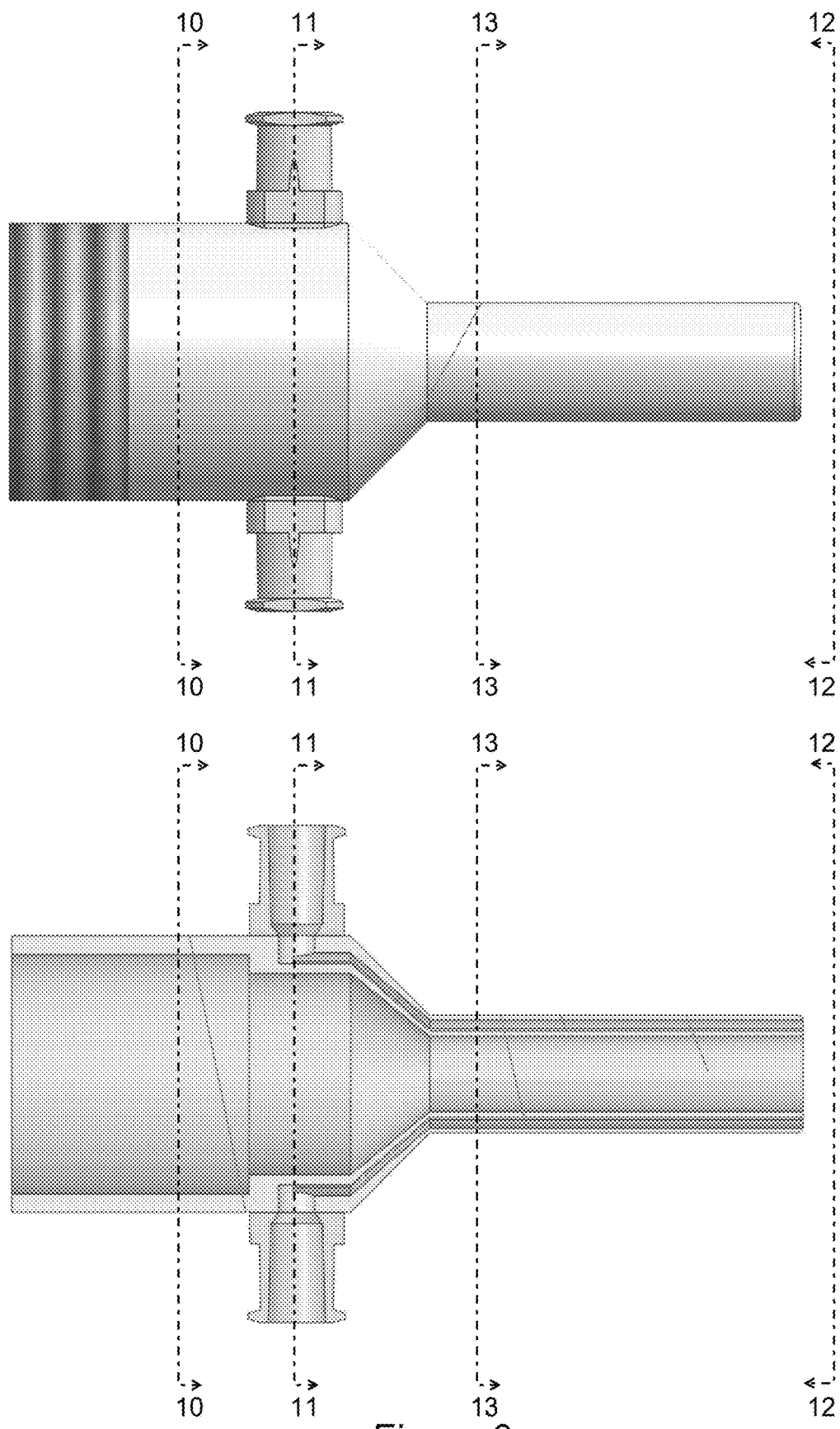
FIG. 9 is a reproduction of FIGS. 7 and 8, with lines added to show where cross-sectional views are taken.

FIG. 9 is a reproduction of FIGS. 7 and 8, with lines added to show where cross-sectional views are taken for FIGS. 10, 11, 12, and 13.

Figure 10:
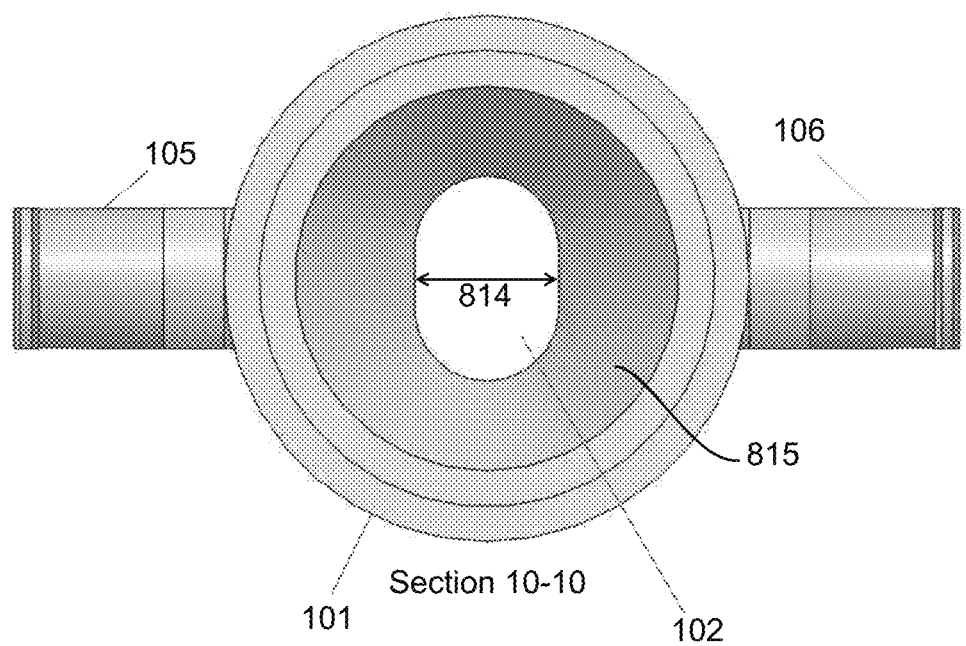
FIG. 10 is a cross-sectional view taken at line 10-10 from FIG. 9.
Figure 11:
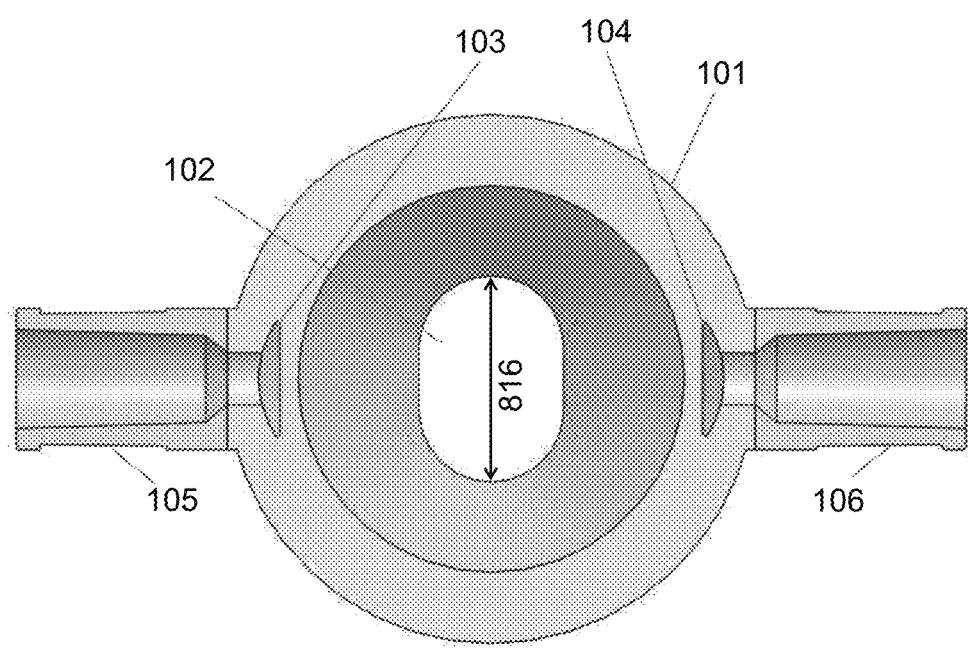
FIG. 11 is a cross-sectional view taken at line 11-11 from FIG. 9.

FIG. 10 is a cross-sectional view taken above the Luer-style ports 105 and 106 looking in the distal direction of the instrument. The cross-sectional view of FIG. 11 faces in the same direction but is taken at a longitudinal position that bisects the Luer-style ports 105 and 106. From the perspectives of FIGS. 10 and 11, it can be clearly seen that the central lumen 102 does not have a circular cross-section. It has a width 814 and length 816, where the length is greater than the width. The cross-sectional shape may be referred to as pill-shaped or oblong. Ellipsoid or circular cross-sectional shapes may be acceptable alternatives in some embodiments. As illustrated in the exemplary embodiment depicted by the figures, the central lumen 102 is an ellipsoid that is nominally 6 mm×9 mm with a radius of 3 mm to allow the passage and manipulation of straight surgical instruments up to 5.5 mm in diameter and curved tip instruments (e.g., shaver) that are 4.5 mm in diameter. These dimensions may be increased or decreased accordingly for the use of smaller or larger instruments.

Figure 12:
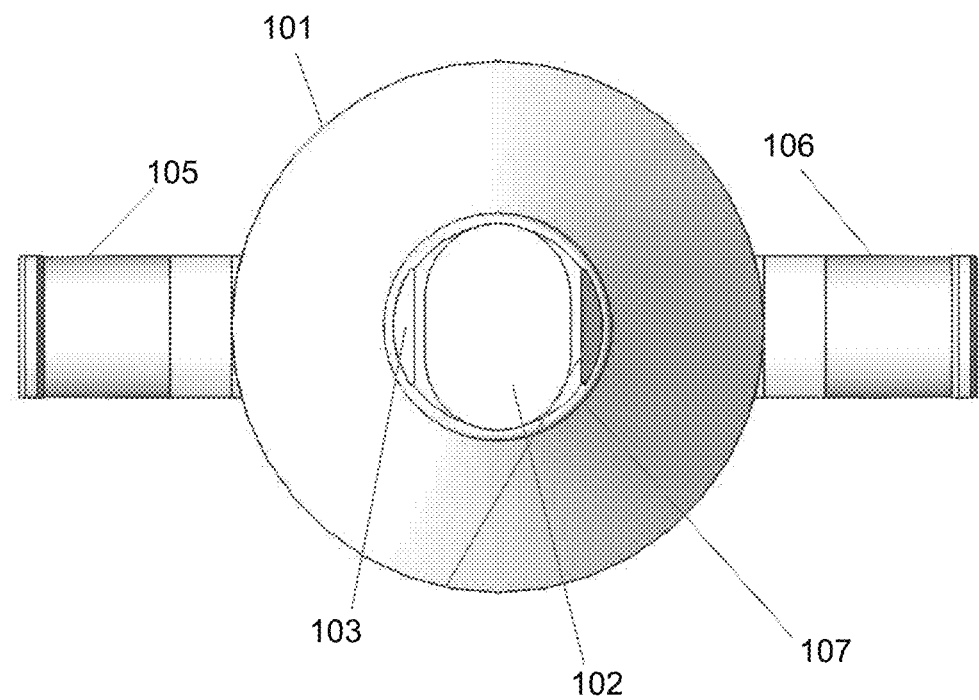
FIG. 12 is a end view taken from the perspective of line 12-12 from FIG. 9.
Figure 13:
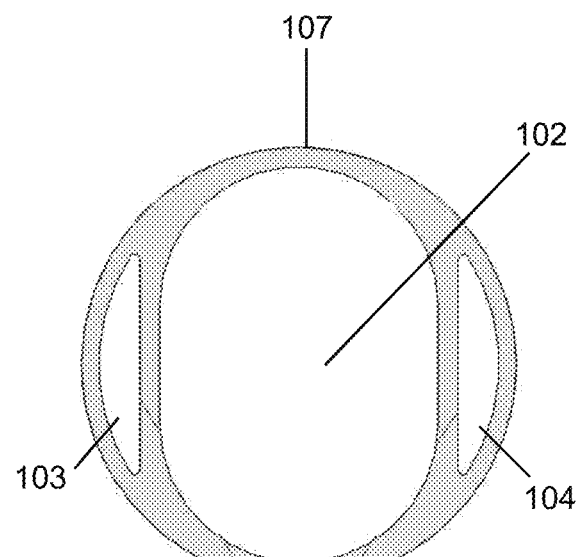
FIG. 13 is a cross-sectional view taken at line 13-13 from FIG. 9.

FIG. 12 is an end view of the cannula housing 101, as viewed from the distal end. FIG. 13 is a cross-sectional view of the cannula shaft 107. These views make apparent the basis for the ellipsoid shape of the central lumen 102 and the length 816 being greater than the width 814, despite the cannula shaft 107 being cylindrical with a circular cross-sectional profile. The cannula shaft 107 is partitioned into three separate passages. In the center is the central lumen 102, sized to permit passage of medical instruments. Unlike convention trocars, central lumen 102 is of a length and cross-sectional such that it allows passage of straight- and curved-tip arthroscopic surgical instruments. On opposite sides of the central lumen are fluid channels 103 and 104. Each of the fluid channels 103 and 104 shares a wall with the central lumen 102.

FIG. 13 show an (enlarged) cross-section of the cannula shaft 107. While the central lumen 102 may or may not be circular as a result of the integration of the fluid channels 103 and 104 within the same structure of the cannula shaft 107, it is readily apparent from the figures that a single, unimpeded cannula is afforded by the design for the passage of surgical instruments. There is no need for irrigation and suction tubules or the like to be passed through the central lumen, avoiding any risk of entanglement or obstruction. The ellipsoid-like central lumen 102 may be dedicated entirely to the passage of surgical instruments, and nothing else, if so desired by the surgeon. Yet, effusion and fluid withdrawal are still available.

The central lumen 102 within the cannula shaft 107 may be fluid filled up to the first multi-leaflet valve. If desired, a positive or negative fluid flow may be supplied within the central lumen through a third port (e.g., a Luer-lock style port) (not shown) to supplement one of either channel 103 and 104. In some embodiments, one (but not both) channels 103 and 104 may be omitted and its function provided by the central lumen 102. That is to say, the central lumen 102 may be used for either effusion or suction of fluid, though obviously not both. In this case one of the Luer-lock style ports would connect to the central lumen 102.

Figure 14:
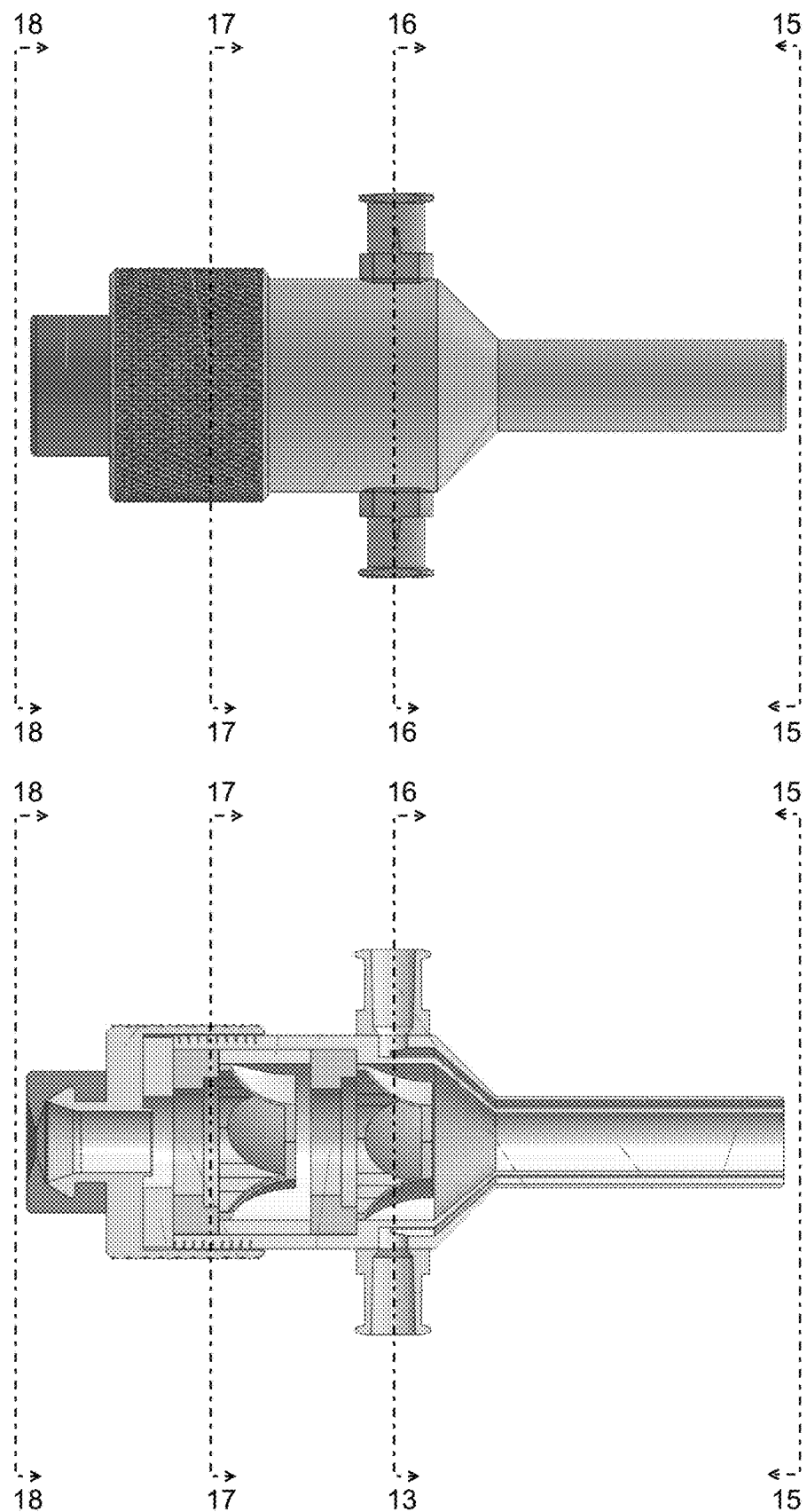
FIG. 14 is a reproduction of FIGS. 2 and 5, with lines added to show where cross-sectional views are taken.
Figure 15:
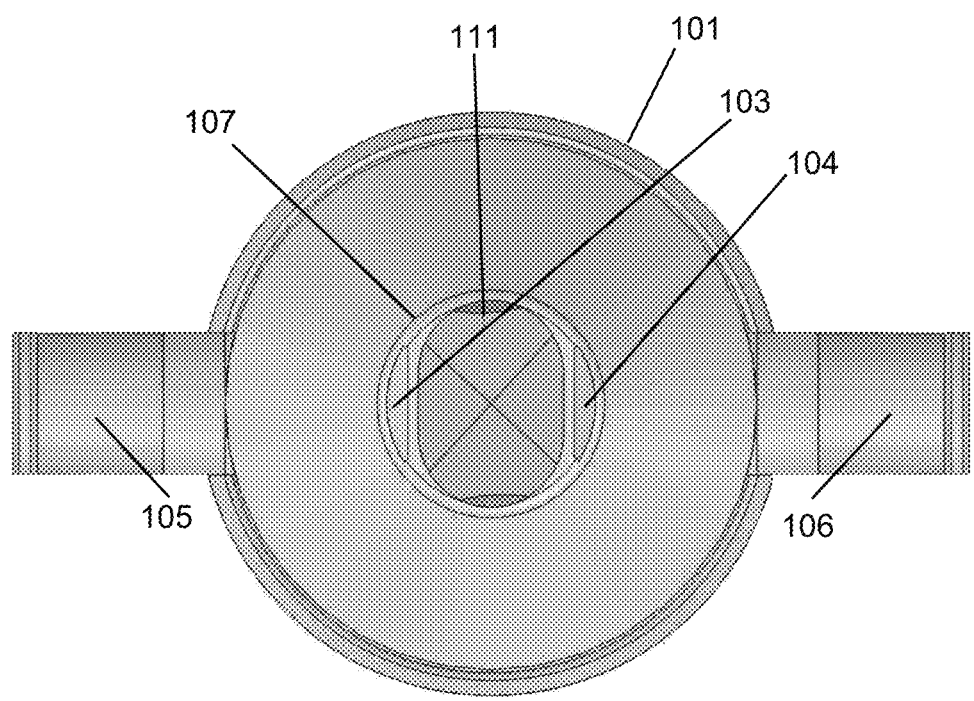
FIG. 15 is an end view taken from the perspective of line 15-15 from FIG. 14.

FIGS. 14 through 18 provide further views of the full assembly, including all components shown in the exploded view of FIG. 4. FIG. 14 is a reproduction of FIGS. 2 and 5, with lines added to show where cross-sectional views are taken for the subsequent figures. FIG. 15 is a view of the MLAC 100 as seen from the distal end. With the internal components included, the multi-leaflet valve 111 is visible from the distal end of the central lumen 102.

Figure 16:
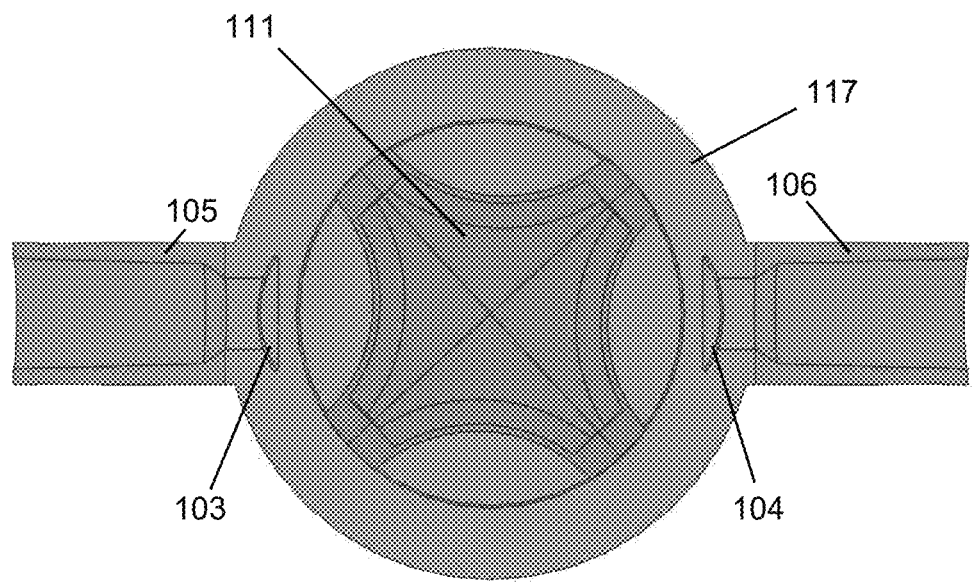
FIG. 16 is a cross-sectional view taken at line 16-16 from FIG. 14.
Figure 17:
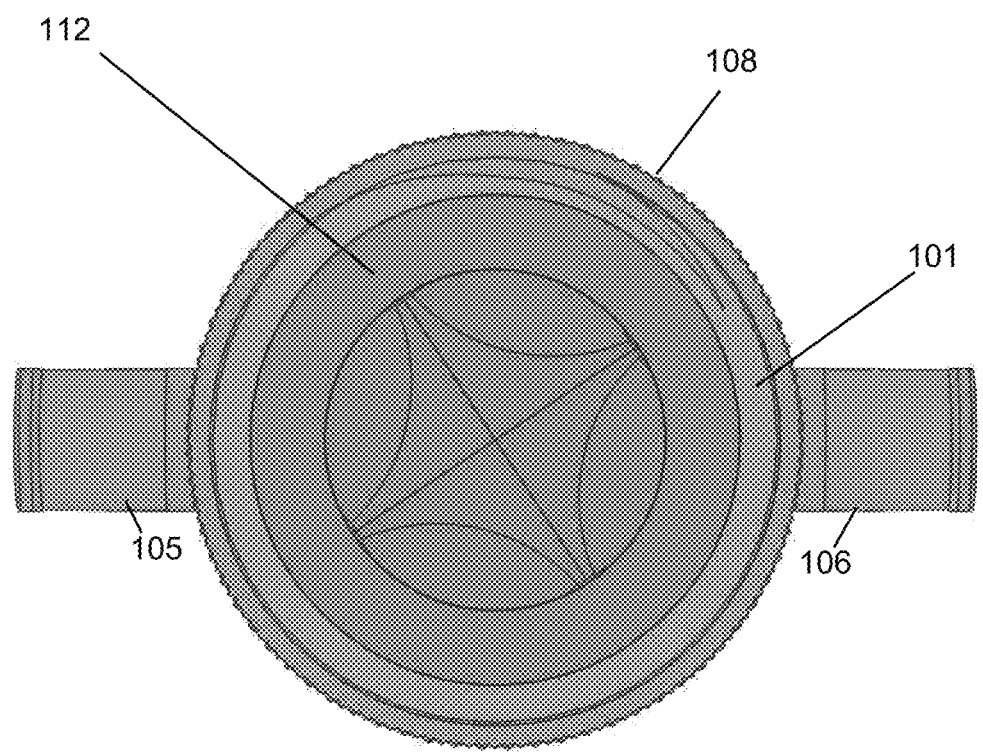
FIG. 17 is a cross-sectional view taken at line 17-17 from FIG. 14.
Figure 18:
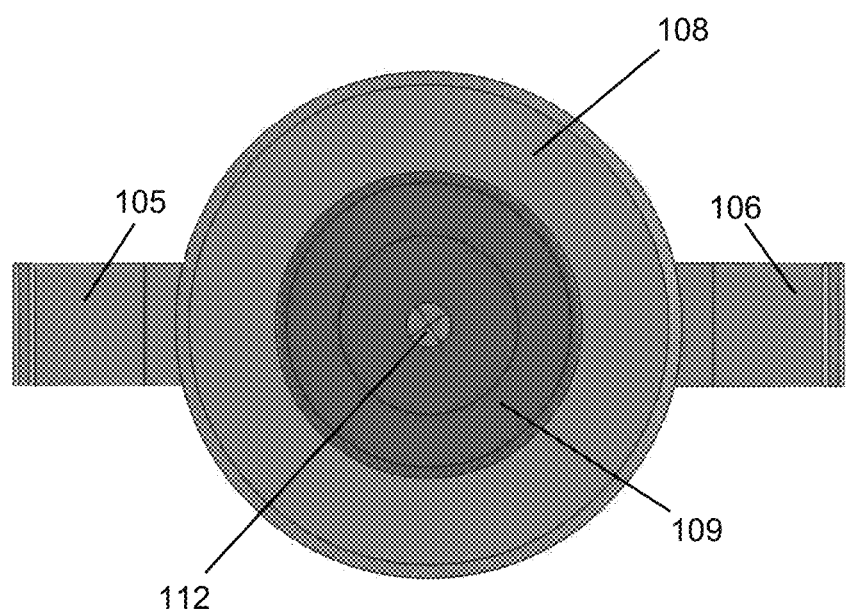
FIG. 18 is a cross-sectional view taken at line 18-18 from FIG. 14.

FIG. 16 is a cross section of the housing taken through Luer-lock style ports 105 and 106. FIG. 17 is a cross section taken further up the MLAC 100, at a position along the end cap 108. FIG. 18 is a view from the proximal end of the MLAC 100.

Representative illustrative methods and materials are herein described; methods and materials similar or equivalent to those described herein can also be used in the practice or testing of the present invention.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be separated from or combined with the features of any of the other several embodiments without departing from the scope or spirit of the present invention. Any recited method can be carried out in the order of events recited or in any other order which is logically possible.

While the invention has been described in terms of exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

REFERENCE NUMBER LISTING 100 multi-lumen arthroscopy cannula
101 cannula housing
102 central lumen
103 fluid channel
104 fluid channel
105 Luer-style port
106 Luer-style port
107 cannula shaft (of cannula housing)
108 end cap
109 dual-tapered diaphragm seal
110 end cap seal
111 multi-leaflet valve
112 multi-leaflet valve
113 valve spacer
114 threading (of end cap)
115 threading (of cannula housing)
116 retention ledge
117 main body (of cannula housing)
118 tapered portion (of main body of cannula housing)
811 inner diameter (of main body)
812 reduced inner diameter (of main body)
813 inner diameter (of tapered portion)
814 width
815 conical surface
816 length

What is claimed is:

1. A multi-lumen arthroscopy cannula (MLAC), comprising a cannula housing that includes a main body and a cannula shaft, the main body containing a series of valves configured to permit passage of straight- and curved-tip arthroscopic surgical instruments while concurrently limiting passage of fluids, wherein material of the cannula shaft partitions an interior of the cannula shaft into a central lumen, irrigation lumen, and suction lumen such that the central lumen, irrigation lumen, and suction lumen are fully separated from one another, wherein the irrigation and suction lumens are arranged on opposite sides of the central lumen and in parallel with the central lumen, wherein the irrigation and suction lumens permit provision of a continuous pressure at a distal end of the central lumen from simultaneous irrigation and suction.

2. The MLAC of claim 1, wherein the series of valves include a first multi-leaflet valve and a second multi-leaflet valve arranged consecutively within the cannula housing, and further comprising a dual-tapered diaphragm seal at an end of the cannula housing.

3. The MLAC of claim 1, wherein each of the irrigation lumen and the suction lumen shares a respective wall with the central lumen that fluidically separates the central lumen from either the irrigation lumen or the suction lumen, the respective wall being of the material of the cannula shaft.

4. The MLAC of claim 1, wherein the irrigation and suction lumens terminate at Luer-lock style ports positioned above the cannula shaft at a base of the main body of the cannula housing.

5. A cannula housing, comprising a main body and a cannula shaft, the main body sized to accommodate a series of valves configured to permit passage of straight- and curved-tip arthroscopic surgical instruments while concurrently limiting passage of fluids, wherein material of the cannula shaft partitions an interior of the cannula shaft into a central lumen, irrigation lumen, and suction lumen such that the central lumen, irrigation lumen, and suction lumen are fully separated from one another, wherein the irrigation and suction lumens are arranged on opposite sides of the central lumen and in parallel with the central lumen, wherein the irrigation and suction lumens permit provision of a continuous pressure at a distal end of the central lumen from simultaneous irrigation and suction.

6. The cannula housing of claim 5, further comprising ports for the irrigation and suction lumens positioned above the cannula shaft.

7. The cannula housing of claim 6, wherein the ports are positioned at a base of the main body of the cannula housing.

8. The cannula housing of claim 7, wherein the ports are Luer-lock style ports positioned on opposite sides of the main body.

9. The cannula housing of claim 5, wherein each of the irrigation lumen and the suction lumen shares a respective wall with the central lumen that fluidically separates the central lumen from either the irrigation lumen or the suction lumen, the respective wall being of the material of the cannula shaft.

10. The cannula housing of claim 5, wherein the irrigation and suction lumens extend through an entirety of the cannula shaft to open at a distalmost end.

11. The cannula housing of claim 5, wherein the irrigation lumen opens at a distal end of the cannula shaft in an irrigation direction that is parallel with a longitudinal center axis of the central lumen that is orientable toward a surgical target.

12. The cannula housing of claim 11, wherein the suction lumen opens at the distal end of the cannula shaft in a suction direction that is parallel with the longitudinal center axis of the central lumen that is orientable toward the surgical target.

13. The cannula housing of claim 5, wherein the central lumen has a cross-sectional shape that is one or more of ellipsoid, oblong, and pill-shaped.

14. The cannula housing of claim 5, wherein a cross-section of the central lumen has a width and a length, where the length of the cross-section is greater than the width of the cross-section.

15. A method of using a multi-lumen arthroscopic cannula (MLAC) during a surgical procedure, the MLAC comprising a cannula housing that includes a main body and a cannula shaft, wherein material of the cannula shaft partitions an interior of the cannula shaft into a central lumen, irrigation lumen, and suction lumen such that the central lumen, irrigation lumen, and suction lumen are fully separated from one another, the method comprising using the central lumen to pass one or more surgical instruments or scopes from a proximal end of the MLAC through and out a distal end of the MLAC, wherein the proximal end is outside the patient and the distal end is positioned at a surgical site inside the patient;

supplying to the surgical site irrigation fluid that exits the distal end of the MLAC from the irrigation lumen in an irrigation direction that is parallel with a longitudinal center axis of the central lumen that is orientable toward a surgical target; and supplying to the surgical site suction at the distal end of the MLAC from the suction lumen in a suction direction that is parallel with the longitudinal center axis of the central lumen.

16. The method of claim 15, wherein the surgical procedure is an arthroscopic procedure of a patient's joint, wherein the method further comprises maintaining joint cavity pressure by controlling flow rates of the irrigation fluid and suction.

17. The method of claim 16, further comprising clearing a surgical field using the supplied irrigation fluid to entrain debris and the supplied suction to remove the entrained debris.

18. The method of claim 15, wherein the one or more surgical instruments or scopes are passed through a series of valves within the cannula housing of the MLAC, the series of valves being configured to permit passage of straight- and curved-tip arthroscopic surgical instruments while concurrently limiting passage of fluids.

19. The method of claim 15, wherein the irrigation fluid enters the MLAC through a first port at a first position above the cannula shaft of the MLAC, and suctioned fluid exits the MLAC through a second port at a second position above the cannula shaft.

20. The method of claim 19, wherein the first and second positions above the cannula shaft are on opposite sides of the main body of the MLAC.

* * * * *